(12) United States Patent
Chen et al.

(10) Patent No.: US 7,557,221 B2
(45) Date of Patent: Jul. 7, 2009

(54) SUBSTITUTED HYDANTOINS

(75) Inventors: Shaoqing Chen, Bridgewater, NJ (US); Nicholas J. S. Huby, Scotch Plains, NJ (US); Norman Kong, West Caldwell, NJ (US); John Anthony Moliterni, Bloomfield, NJ (US); Omar Jose Morales, New Milford, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/186,648

(22) Filed: Aug. 6, 2008

(65) Prior Publication Data

US 2009/0048452 A1  Feb. 19, 2009

Related U.S. Application Data

(60) Provisional application No. 60/956,145, filed on Aug. 16, 2007.

(51) Int. Cl.
*A61K 31/4184* (2006.01)
*C07D 403/06* (2006.01)

(52) U.S. Cl. .................... 548/306.1; 514/394

(58) Field of Classification Search ............... 548/306.1
See application file for complete search history.

(56) References Cited

FOREIGN PATENT DOCUMENTS

| WO | WO 99/01426 | 1/1999 |
|---|---|---|
| WO | WO 99/05117 | 2/1999 |
| WO | WO 01/83478 | 11/2001 |
| WO | WO 2005/009975 | 2/2005 |
| WO | WO 2005/023251 | 3/2005 |
| WO | WO 2006/018188 | 2/2006 |
| WO | WO 2006/029862 | 3/2006 |
| WO | WO 2006/124780 | 11/2006 |

OTHER PUBLICATIONS

Hyun et al., J. Liq. Chrom. Rel. Technol., 25, pp. 573-588 (2002).
Böhme et al., J. Med. Chem., 23, pp. 405-412 (1980).
Salituro et al., J. Am. Chem. Soc., 112, pp. 760-770 (1990).
Shimizu et al., J. Chem. Soc. Chem. Commun., 867-868 (1986).
Chemical Abstract Service XP002428310, 1931.

*Primary Examiner*—Laura L. Stockton
(74) *Attorney, Agent, or Firm*—George W. Johnston; Patricia S. Rocha-Tramalon; David E. Wildman

(57) ABSTRACT

This invention relates to compounds of formula I:

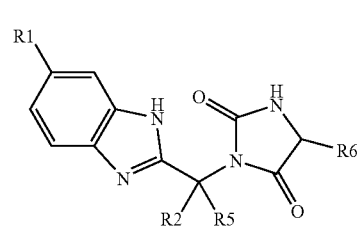

or pharmaceutically acceptable salts thereof,
wherein R1, R2, R3, R4, R5, and R6 are described in this application. These compounds inhibit the enzymes MEK 1 and MEK2, protein kinases that are components of the MAP kinase signal transduction pathway and as such the compounds will have anti-hyperproliferative cellular activity.

10 Claims, No Drawings

SUBSTITUTED HYDANTOINS

PRIORITY TO RELATED APPLICATIONS

This application claims the benefit of U.S. Provisional Application No. 60/956,145, filed Aug. 16, 2007, which is hereby incorporated by reference in its entirety.

FIELD OF THE INVENTION

The present invention relates to hydantoin derivatives and their use as inhibitors of the two protein kinases commonly known as MEK1 and MEK2 for the treatment of human diseases such as cancer. MEK is a commonly used abbreviation for MAP kinase/ERK kinase which is in turn an abbreviation for mitogen activated protein/extracellular signal regulated kinase kinase. MEK is also sometimes referred to as MAPK kinase or MAP kinase kinase.

BACKGROUND OF THE INVENTION

Cancer is a disease characterized by the proliferation of malignant cells and tumors which have the potential for unlimited growth, local expansion and systemic metastasis. This uncontrolled growth is frequently derived from abnormalities in the signal transduction pathways and the response to various growth factors, which differ from those found in normal cells. The abnormalities include changes in the intrinsic activity or in the cellular concentration of one or more signaling proteins in the signaling cascades. These changes are frequently caused by genetic mutations or overexpression of intracellular signaling proteins which can lead to spurious mitogenic signals within the cells.

The mitogen activated protein (MAP) kinase pathway represents one of the best characterized signaling pathways involved in the development and progression of human cancers. This pathway, via the Ras/Raf/MEK/ERK signal cascade, is responsible for transmitting and amplifying mitogenic signals from the cell surface to the nucleus where activated transcription factors regulate gene expression and determine cell fate. The constitutive activation of this pathway is sufficient to induce cellular transformation. Dysregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers. The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2) which in turn phosphorylate ERK1 and ERK2 (extracellular signal-regulated kinases 1 and 2) on both tyrosine-185 and threonine-183. Activated ERK1 and ERK2 translocate and accumulate in the nucleus, where they can phosphorylate a variety of substrates, including transcription factors that control cellular growth and survival. Given the importance of the Ras/Raf/MEK/ERK pathway in the development of human cancers, the kinase components of this signaling cascade are emerging as potentially important targets for the modulation of disease progression in cancer and other proliferative diseases.

MEK1 and MEK2 are members of a larger family of dual-specificity kinases (MEK1-7) that phosphorylate threonine and tyrosine residues of various MAP kinases. MEK1 and MEK2 are encoded by distinct genes, but they share high homology (80%) both within the C-terminal catalytic kinase domains and most of the N-terminal regulatory region. Oncogenic forms of MEK1 and MEK2 have not been found in human cancers, but constitutive activation of MEK has been shown to result in cellular transformation.

In addition to Raf, MEK can also be activated by other oncogenes as well. So far, the only known substrates of MEK1 and MEK2 are ERK1 and ERK2. This unusual substrate specificity in addition to the unique ability to phosphorylate both tyrosine and threonine residues places MEK1 and MEK2 at a critical point in the signal transduction cascade which allows it to integrate many extracellular signals into the MAPK pathway.

Previously reported studies with the MEK inhibitor 2-(2-chloro-4-iodo-phenylamino)-N-cyclopropylmethoxy-3,4-difluoro-benzamide, also known as CI-1040 (PCT publication No. WO 99/01426) provide further evidence that MEK1 and MEK2 represent an attractive target for pharmacological intervention in cancer or other human diseases characterized by the hyperactivity of MEK and diseases regulated by the MAPK pathway.

Substituted hydantoins have previously been reported as glucokinase activators (PCT publication No. WO 01/83478).

SUMMARY OF THE INVENTION

This invention relates to compounds of formula I:

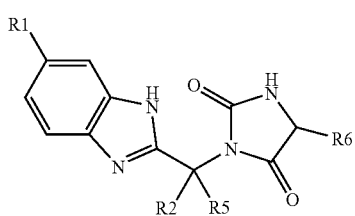

or pharmaceutically acceptable salts thereof, where R1, R2, R3, R4, R5, and R6 are described in this application. These compounds inhibit the enzymes MEK 1 and MEK2, protein kinases that are components of the MAP kinase signal transduction pathway and as such the compounds will have anti-hyperproliferative cellular activity.

DETAILED DESCRIPTION OF THE INVENTION

The present invention is directed to compounds of formula I:

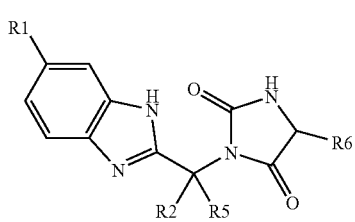

where:
R1 is selected from the group consisting of halogen, ethynyl, and cycloalkyl;
R2 is selected from the group consisting of hydrogen and CH(R3)(R4);
R3 is selected from the group consisting of lower alkyl, lower alkoxy, optionally substituted aryl, and optionally substituted heteroaryl;
R4 is selected from the group consisting of hydrogen and lower alkyl;
R5 is hydrogen or, taken together with R2 and the carbon to which R2 and R5 are attached, forms lower cycloalkyl; and
R6 is selected from the group consisting of hydrogen, lower alkyl, lower cycloalkyl, optionally substituted aryl, and optionally substituted heteroaryl;

and pharmaceutically acceptable salts or esters thereof.

In another aspect, the invention is directed to compounds of formula I where
R1 is selected from the group consisting of bromo, iodo, ethynyl, and C3 to C6 cycloalkyl;
R2 is selected from the group consisting of hydrogen and CH(R3)(R4);
R3 is selected from the group consisting of C1 to C3 alkyl, C1 to C3 alkoxy, optionally substituted phenyl, and optionally substituted heteroaryl, wherein the heteraryl group contains at least one sulfur atom or nitrogen atom;
R4 is selected from the group consisting of hydrogen and C1 to C3 alkyl;
R5 is hydrogen or, taken together with R2 and the carbon to which R2 and R5 are attached, forms lower cycloalkyl; and
R6 is selected from the group consisting of hydrogen, lower alkyl, lower cycloalkyl, optionally substituted aryl, and optionally substituted heteroaryl;

and pharmaceutically acceptable salts or esters thereof.

In one aspect the invention is directed to compounds of formula I where R1 is iodo, bromo, ethynyl, or cyclopropyl and pharmaceutically acceptable salts or esters thereof.

In another aspect the invention is directed to compounds of formula I where R2 is CH(R3)(R4) and R3 is methyl, methoxy, phenyl, 4-fluorophenyl, 4-methoxyphenyl, or thiophene and pharmaceutically acceptable salts or esters thereof.

In another aspect the invention is directed to compounds of formula I where R2 is CH(R3)(R4) and R4 is hydrogen or methyl and pharmaceutically acceptable salts or esters thereof.

In another aspect the invention is directed to compounds of formula I where R5, taken together with R2 and the carbon to which R2 and R5 are attached, forms lower cycloalkyl and pharmaceutically acceptable salts or esters thereof.

In another aspect the invention is directed to compounds of formula I where R5, taken together with R2 and the carbon to which R2 and R5 are attached, forms cyclopropyl and pharmaceutically acceptable salts or esters thereof.

In another aspect the invention is directed to compounds of formula I where R6 is 2-propyl, cyclohexyl, phenyl, 4-methoxyphenyl, 4-(O(CH2)2OH)-phenyl, 4-(O(CH2)2OCH3)-phenyl, 4-(OCH2C(O)N(CH3)2)-phenyl, 4-(OCH2C(O)N((CH2)2OH)2)-phenyl and pharmaceutically acceptable salts or esters thereof.

In another aspect the invention is directed to compounds of formula I where
R1 is cyclopropyl, acetylene, iodo, or bromo;
R2 is H or CH(R3)(R4);
R3 is methyl, methoxy, phenyl, 4-fluorophenyl, 4-methoxyphenyl, or 2-thiophenyl;
R4 is hydrogen or methyl;
R5 is hydrogen or, taken together with R2 and the carbon to which they are attached, is cyclopropyl;
R6 is hydrogen, 2-propyl, cyclohexyl, phenyl, 4-methoxyphenyl, 4-(O(CH2)2OH)-phenyl, 4-(O(CH2)2OCH3)-phenyl, 4-(OCH2C(O)N(CH3)2)-phenyl, or 4-(OCH2C(O)N((CH2)2OH)2)-phenyl and pharmaceutically acceptable salts or esters thereof.

Preferred compounds of the invention are as set forth in the Examples below.

"Aryl" means a monovalent, monocyclic or bicyclic, aromatic carbocyclic or heterocyclic radical, preferably a 5 to 10 member aromatic ring system. Preferred aryl groups include, but are not limited to, phenyl, naphthyl, tolyl, xylyl, thienyl, furyl, indolyl, pyrrolyl, pyridinyl, oxy-pyridinyl, pyrazinyl, oxazolyl, thiaxolyl, quinolinyl, pyrimidinyl, imidazole and tetrazolyl. Aryl groups containing heteroatoms such as N, O, and S are also referred to herein as "heteroaryl" groups. Aryl groups can be optionally mono-, di- or tri-substituted by, for example, lower alkyl, cycloalkyl, e.g., cyclopropyl, trihalolower alkyl, e.g., trifluoromethyl, hydroxyl, alkoxy, especially lower alkoxy, mono or dihydroxyl-substituted alkoxy, acetamido, methoxyacetamido, dimethylaminoacetamido, halogen, e.g., fluoro, chloro, or bromo, aniline derivatives, amide derivatives of the aniline derivatives and methanesulfonyl. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Heteroatom" means an atom selected from N, O and S.

"Heterocyclyl" means a group having four to six carbon atoms and at least one heteroatom.

"Alkoxy or lower alkoxy" refers to any of the above lower alkyl groups attached to an oxygen atom. Typical lower alkoxy groups include methoxy, ethoxy, isopropoxy or propoxy, butyloxy, cyclopropyl methoxy, and the like. Further included within the meaning of alkoxy are multiple alkoxy side chains, e.g. ethoxy ethoxy, methoxy ethoxy, methoxy ethoxy ethoxy, methyl oxetanyl methoxy and the like. Also included are substituted alkoxy side chains, e.g., hydroxyethoxy, dihydroxypropoxy, dimethylamino ethoxy, diethylamino ethoxy, phosphoryl methoxy, dimethoxy-phosphoryl methoxy, carbamoyl methoxy, methyl and dimethyl carbamoyl methoxy, carbamoyl ethoxy, methyl and dimethyl carbamoyl ethoxy, azetidinyl carbamoyl ethoxy, oxopyrrolidinyl ethoxy, bishydroxyethylcarbamoyl methoxy, morpholinyl methoxy, morpholinyl ethoxy, piperazinyl methoxy, piperazinyl ethoxy, lower-alkyl piperazine ethoxy, oxo-pyrrolidinyl ethoxy, and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard Hans ed. (Elsevier, 1985). See also, Ansel et. al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount" or "effective amount" means an amount of at least one designated compound that significantly inhibits proliferation and/or prevents differentiation of a human tumor cell, including human tumor cell lines.

The compounds of the present invention are useful in the treatment or control of cell proliferative disorders such as inflammatory/autoimmune disorders, e.g., restenosis, cognitive disorders, e.g., dementia and Alzeheimer's disease, CNS disorders, e.g., neuropathic pain and, in particular, oncological disorders. These compounds and formulations containing said compounds may be useful in the treatment or control of solid tumors, such as, for example, breast, colon, lung and prostate tumors.

The compounds of formula I as well as their salts have at least two asymmetric carbon atoms and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

Reaction Scheme

The compounds claimed in the present invention (compounds of general formula 1) may be prepared by the general route shown in scheme 1.

Scheme 1: General route for preparation of benzimidazole derivatives 1.

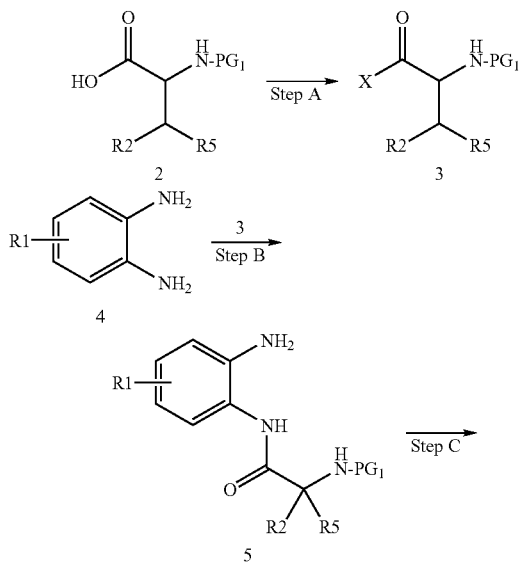

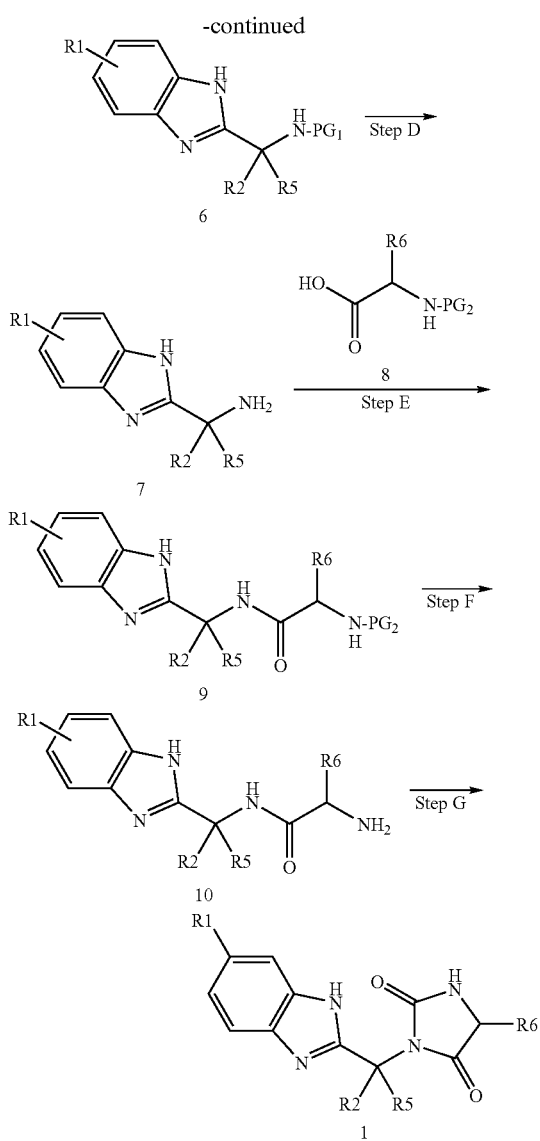

Step A: A compound containing an α-amino acid functional grouping of general formula 2 is converted in to a reactive acylating species of general formula 3 which is suitable for use in step B of the synthetic sequence. Step A is most conveniently performed on an α-amino acid which bears a protecting group (PG1) on the α-amine nitrogen. A suitable choice for protecting group PG1 is one which renders the α-amine nitrogen inert to the reaction conditions employed during steps A, B and C of the synthetic sequence but which may be removed during step D of the synthetic sequence without causing undesired modifications to the rest of the compound when exposed to the conditions required for the removal of the protecting group. Preferred choices for protecting group PG1 may be made by reference to organic chemistry text books (e.g. Greene's Protective Groups in Organic Synthesis Fourth Edition, Peter G. M. Wuts and Theodora W. Greene, ISBN 0-471-69754-0), the original chemistry literature or would be known to one knowledgeable in the art of organic synthesis. In particular carbamate based protecting groups, e.g. tert-butyloxycarbonyl are preferred but other amine protecting groups may also be effective.

The choice of which reactive acylating agent of general formula 3 to form is dependent upon both compatibility with potentially reactive functional groups present elsewhere in compounds of general formula 3 and the reactivity and selectivity of the acylating agent of general formula 3 for acylation of the 1,2-diaminobenzene derivative of general formula 4 with formation of the desired amide bond present in compound of general formula 5. Typical reactive acylating agents which may be employed in step B are acyl halides (3, X=halogen) and acid anhydrides (3, X=O—C(O)R). Preferred choices for the acylating agents of general formula 3 are the acyl halides, in particular acyl fluorides (3, X=fluorine). Additional choices for acylating agents of general formula 3 may also be suitable for use in step B and would be apparent to one knowledgeable in the art of organic synthesis.

In the case where compounds of general formula 2 contain a chiral center at the α-carbon, the preferred stereochemistry is S.

Step B: A 1,2-diaminobenzene derivative of general formula 4 is combined with a pre-formed acylating agent of general formula 3 to form a 2-aminoanilide derivative of general formula 5.

It will be apparent to one skilled in the art of organic synthesis that by use of known peptide coupling reaction techniques it may be possible to prepare 2-aminoanilide derivatives of general formula 5 directly from compounds of general formula 2 and general formula 4 without having to pre-form a reactive acylating agent of general formula 3. Typical peptide coupling reagents which may be employed for the direct conversion of compounds of general formula 2 and general formula 4 to compounds of general formula 5 include diimide based reagents e.g. dicyclohexylcarbodiimide, (3-dimethylamino-propyl)-ethyl-carbodiimide hydrochloride; or uronium based reagents, e.g. O-benzotriazol-1-yl-N,N,N',N'-tetramethyluronium hexaflurorophosphate. Alternative peptide coupling reagents may also effective in performing this conversion. Selection of alternative peptide coupling reagents may be made by reference to the original chemistry literature or would be known to one knowledgeable in the art of organic synthesis.

It will also be apparent to one skilled in the art of organic synthesis that when an additional substituent or substituents is/are present (denoted as R1 in compound of general formula 4 and subsequent derivatives) the 2-aminoanilide derivatives of general formula 5 resulting from step B can be formed as a mixture of regioisomers. Separation of the regioisomeric forms of compounds of general formula 5 is not necessary or productive as the subsequent step in the synthetic scheme (step C) results in the formation of compounds of general formula 6 with only one possible regioisomer possible no matter the regiochemistry of the starting 2-aminoanilide derivatives of general formula 5.

Step C: 2-Aminoanilide derivatives of general formula 5 can be cyclized to form benzimidazole derivatives of general formula 6. Cyclization occurs between the amino group at the 2-position of the phenyl ring and the carbonyl group of the anilide and is accompanied by loss of water. Heating of 2-aminoanilide derivatives of general formula 5 in glacial acetic acid is an efficient way of performing this cyclization to afford benzimidazole derivatives of general formula 6 which does not cause appreciable removal of protecting groups such as tert-butyloxycarbonyl.

Benzimidazole derivatives of general formula 6 are depicted in scheme 1 as a single tautomer in the imidazole for ease of representation while in actuality the benzimidazole will be present as an equilibrium mixture of the 2 possible tautomers of the imidazole ring. Tautomerization in imidazole rings is a phenomena well known in the field of organic chemistry. Tautomerism of the imidazole ring also results in both potentially regioisomeric forms of compounds of general formula 5 giving rise to compounds of general formula 6 as single regioisomers but which are tautomeric in the imidazole ring.

Step D: This step in the synthetic sequence entails the removal of protecting group PG1 from compounds of general formula 6 to form free amine containing compounds of general formula 7 in preparation for subsequent elaboration. Choice of protecting group for PG1 and conditions to best achieve its removal may be made by reference to standard organic chemistry text books (as cited in Step A), the original chemistry literature or would be known to one knowledgeable in the art of organic synthesis. This choice is influenced by what other potentially reactive functional groups are present in compounds of general formula 6 and the requirement of avoiding undesired reactions elsewhere in the starting material or product of the reaction, compounds of general formulae 6 and 7 respectively. In the case where the amine protecting group PG1 present in compounds of general formula 5 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the amine of general formula 7, from which the free amine of general formula 7 can be liberated after treatment with base.

The benzimidazole moiety in compounds of general formula 6 and 7 are also subject to reversible salt formation under acidic conditions, with the unionized benzimidazole being reformed upon treatment with a sufficient amount of base to neutralize the salt form.

Step E: Compounds of general formula 9 are obtained by combining amines of general formula 7 with a compound containing an α-amino acid functional grouping. Step E is most conveniently performed on compounds of general formula 8 which contain an α-amino acid which bears a protecting group (PG2) on the α-amine nitrogen. The criteria for choice of the protecting group PG2 are the same as described for the choice of protecting group PG1 in step B. In particular carbamate based protecting groups, e.g. tert-butyloxycarbonyl are preferred but other amine protecting groups may also be effective.

In the case where compounds of general formula 8 contain a chiral center at the α-carbon, the preferred stereochemistry is R.

Step F: This step in the synthetic sequence entails the removal of protecting group PG2 from compounds of general formula 9 to form free amine containing compounds of general formula 10 prior to completion of the synthetic sequence. Choice of protecting group for PG2 and conditions to best achieve its removal may be made by reference to standard organic chemistry text books (as cited in Step A), the original chemistry literature or would be known to one knowledgeable in the art of organic synthesis. This choice is influenced by what other potentially reactive functional groups are present in compounds of general formula 9 and the requirement of avoiding undesired reactions elsewhere in the starting material or product of the reaction, compounds of general formulae 9 and 10 respectively. In the case where the amine protecting group PG2 present in compounds of general formula 9 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the compound of general formula 10, from which the free amine of general formula 10 can be liberated after treatment with base.

The benzimidazole moiety in compounds of general formula 9 and 10 are also subject to reversible salt formation under acidic conditions, with the unionized benzimidazole being reformed upon treatment with a sufficient amount of base to neutralize the salt form.

Step G: Compounds of general formula 1 as are claimed in the present invention can be obtained from compounds of general formula 10 by cyclization in the presence of phosgene or equivalent reagent, i.e. a carbonyl group directly attached to two displaceable groups. A preferred reagent for effecting the cyclization of compounds of general formula 10 to compounds of general formula 1 is trichloromethyl chloroformate which functions in the reaction mixture as two equivalents of phosgene. Cyclization of compounds of general formula 10 with trichloromethyl chloroformate is generally rapid and is typically performed at low temperature (<0° C.) and in the presence of a carefully controlled amount of base to neutralize acid formed during the cyclization but to avoid unnecessary isomerization of the potentially labile chiral center on the newly formed hydantoin ring.

It will be apparent to one knowledgeable in the art of organic synthesis that when one or more of the substituents labeled R1 through R6 in the compounds shown in scheme 1 are in and of themselves chemically reactive groups, or contain chemically reactive groups, then additional modification of the compounds of general formula 1 through 10 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in scheme 1. Alternatively, if the newly elaborated group is not chemically inert or can interfere with the remaining steps in the synthetic sequence it may be necessary to temporarily mask the reactive functional group with an appropriate protecting group. If a protecting group is introduced which is not required in the final compound of general structure 1 then it may either be removed under the conditions remaining in the synthetic sequence shown in scheme 1 or by introduction of an additional deprotection step into the synthetic sequence depending upon the nature of the protecting group employed.

Compound $IC_{50}$ determination in MEK cascade assay

The evaluation of the compounds as MEK inhibitor was performed in a bead-based FP assay termed IMAP assay with MEK cascade components. In brief, the assay was performed in a reaction solution containing 10 mM HEPES, pH 7.0, 10 mM $MgCl_2$, 50 mM NaCl, 0.1 mM $NaVO_4$, and 1 m M DTT in the presence of 50 μM ATP, 1 nM c-RAF, 22.5 nM MEK, 90.5 nM ERK, and 0.5 μM FITC-labeled ERK (FITC-Aca-Ala-Ala-Ala-Thr-Gly-Pro-Leu-Ser-Pro-Gly-Pro-Phe-Ala-NH2). C-RAF, MEK, ERK and the ERK peptide substrates were added sequentially into the reaction buffer. Activated c-Raf phosphorylates MEK, activated MEK phosphorylates ERK, and subsequently activated ERK phosphrylates its peptide substrate. The FITC-labeled peptide substrates, when phosphorylated by the kinase, bind to nanoparticles derivatized with trivalent metal cations through a metal-phospholigand interaction. The result of this bound fluoresceinated phosphorylated product is an increase in polarization signal caused by a decrease in the molecular mobility of the bound product. Ten-point serial dilutions of the compounds were added into the MEK cascade assays before mixing with ERK and ERK peptide substrates. The reaction mixture was incubated for 1 hr at 37° C. The reaction was stopped by transferring 2 μl of reaction mixture to 30 μl of 1:400 IMAP beads buffer, then was incubated overnight at room temperature for binding of IMAP beads. The IMAP assay was performed in a 384-well plate format. The changes in fluorescence polarization were measured by LJL instrument at 485 nm for excitation and 530 for emission. Polarization value (MP) was calculated as the following:

$$(MP)=1000\times(\text{intensity vertical}-\text{intensity horizontal})/(\text{intensity vertical}+\text{intensity horizontal}).$$

Compound IC50 values are determined from inter-plate triplicate sets of data. Data were analyzed by using XLfit4 and fitting data to 4 Parameter Logistic Model (Sigmoidal Dose-Response Model), equation $Y=(A+((B-A)/(1+((C/x)^{\wedge}D))))$, where A and B are enzyme activity in the presence of no and infinite inhibitor compound respectively, C is the IC50 and D is the hill constant of the compound response.

The compounds of formula I set forth in the Examples below exhibit IC50 values of less than 7 micromolar in the above assay.

EXAMPLE 1

(R)-5-[4-(2-Hydroxy-ethoxy)-phenyl]-3-[(S)-1-(6-iodo-1H-benzoimidazol-2-yl)-2-phenyl-ethyl]-imidazolidine-2,4-dione

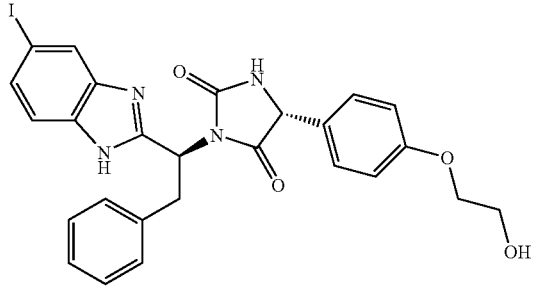

Step 1-A: To a solution of (S)-2-tert-butoxycarbonylamino-3-phenyl-propionic acid (1.0 g, 3.77 mmol) in dichloromethane (18 mL) at −35° C. was added dry pyridine (320 μL, 3.96 mmol) and cyanuric fluoride (477 μL, 5.65 mmol) under an atmosphere nitrogen. The mixture was stirred for 1.5 hours while maintaining the temperature between −35 and −25° C. Ice was added to the reaction mixture and the mixture was stirred for 15 minutes. The organic layer was separated and the aqueous layer extracted with dichloromethane (2×10 mL). The combined organic extracts were washed with ice cold water (15 mL), dried over sodium sulfate, filtered and concentrated in vacuo to give ((S)-1-fluorocarbonyl-2-phenyl-ethyl)-carbamic acid tert-butyl ester which was used in the subsequent step without further purification.

Step 1-B: To a solution of 4-iodo-benzene-1,2-diamine (793 mg, 3.39 mmol) in dry tetrahydrofuran (19 mL) was added a solution of ((S)-1-fluorocarbonyl-2-phenyl-ethyl)-carbamic acid tert-butyl ester (~3.77 mmol) in dry tetrahydrofuran (10 mL) and a catalytic amount of dimethyl-pyridin-4-yl-amine. The mixture was heated to reflux under an atmosphere of nitrogen for 7 hours and then cooled to ambient temperature. The reaction mixture was concentrated in vacuo and the residue taken up in ethyl acetate. The organic solution was washed with water (1×20 mL), brine, dried over sodium sulfate, filtered and concentrated in vacuo. The crude product was purified by chromatography over silica gel gradient eluted from 20 to 50% v/v ethyl acetate/hexanes to give a mixture of regioisomers, [(S)-1-(2-amino-4-iodo-phenylcarbamoyl)-2-phenyl-ethyl]-carbamic acid tert-butyl ester and [(S)-1-(2-amino-5-iodo-phenylcarbamoyl)-2-phenyl-ethyl]-carbamic acid tert-butyl ester (1.1 g, 60%).

HR-MS: calcd for $C_{20}H_{24}IN_3O_3$ [M+H$^+$] 482.0935, found 482.0931.

Step 1-C: The mixture of regioisomers from step 2 {[(S)-1-(2-amino-4-iodo-phenylcarbamoyl)-2-phenyl-ethyl]-carbamic acid tert-butyl ester and [(S)-1-(2-amino-5-iodo-phenylcarbamoyl)-2-phenyl-ethyl]-carbamic acid tert-butyl ester} (1.0 g, 2.08 mmol) were dissolved in glacial acetic acid (30 mL) and heated to 65° C. for 1 hour. The reaction was cooled, concentrated in vacuo, basified with 10% w/v aqueous sodium hydrogen carbonate solution and extracted with ethyl acetate (2×20 mL). The organic extracts were combined, washed with brine, dried over sodium sulfate, filtered and concentrated in vacuo. The crude product was purified by chromatography over silica gel eluted with 20% v/v ethyl acetate/hexanes to give [(S)-1-(5-iodo-1H-benzoimidazol-2-yl)-2-phenyl-ethyl]-carbamic acid tert-butyl ester as a mixture of tautomers (950 mg, 99%).

HR-MS: calcd for $C_{20}H_{22}IN_3O_2$ [M+H$^+$] 464.0830, found 464.0823.

Step 1-D: To a solution of [(S)-1-(5-iodo-1H-benzoimidazol-2-yl)-2-phenyl-ethyl]-carbamic acid tert-butyl ester (1.0 g, 2.16 mmol) in dichloromethane (11 mL) at 0° C. under an atmosphere of nitrogen was added trifluoroacetic acid (6.0 mL, 81 mmol) and the mixture stirred at 0° C. with warming to room temperature over 2 hours. The reaction mixture was concentrated in vacuo then basified with saturated aqueous sodium hydrogen carbonate solution and extracted with ethyl acetate (2×25 mL). The organic extracts were combined, washed with brine, dried over sodium sulfate, filtered and concentrated in vacuo to give (S)-1-(5-iodo-1H-benzoimidazol-2-yl)-2-phenyl-ethylamine which was used in the subsequent step without further purification (750 mg, 96%).

HR-MS: calcd for $C_{15}H_{14}IN_3$ [M+H$^+$] 364.0305, found 364.0302.

Step 1-E: To a solution of (S)-1-(5-iodo-1H-benzoimidazol-2-yl)-2-phenyl-ethylamine (161 mg, 0.44 mmol) in N,N-dimethylformamide (3 mL) at 0° C. was added (R)-tert-butoxycarbonylamino-[4-(2-tert-butoxy-ethoxy)-phenyl]-acetic acid (179 mg, 0.49 mmol) (prepared as described below), N,N-diisopropylethylamine (310 μL, 1.77 mmol), N-hydroxybenzotriazole (72 mg, 0.53 mmol), O-benzotriazol-1-yl-N,N,N',N'-tetramethyluronium hexafluorophosphate (202 mg, 0.53 mmol) and a catalytic amount of dimethyl-pyridin-4yl-amine. The mixture was stirred under an atmosphere of nitrogen with warming to room temperature over 3 hours. The reaction was poured into ice/water (20 mL) and extracted with ethyl acetate (2×20 mL). The organic extracts were combined, washed with brine, dried over sodium sulfate, filtered and concentrated in vacuo. The crude product was purified by chromatography over silica gel gradient eluted with 20 to 35% v/v ethyl acetate/hexanes to give {(R)-[4-(2-tert-butoxy-ethoxy)-phenyl]-[(S)-1-(5-iodo-1H-benzoimidazol-2-yl)-2-phenyl-ethylcarbamoyl]-methyl}-carbamic acid tert-butyl ester (260 mg, 83%).

HR-MS: calcd for $C_{34}H_{41}IN_4O_5$ [M+H$^+$] 713.2195, found 713.2184.

Preparation of (R)-tert-butoxycarbonylamino-[4-(2-tert-butoxy-ethoxy)-phenyl]-acetic acid: A 3 liter, 3-necked round bottom flask equipped with a mechanical stirrer, temperature probe, addition funnel and nitrogen bubbler was charged with (R)-tert-butoxycarbonylamino-(4-hydroxy-phenyl)-acetic acid (67.9 g, 254 mmol) (Salituro, G. M.; Townsend, C. A. *J. Am. Chem. Soc.* 1990, 112, 760-770) in 1-methyl-pyrrolidin-2-one (225 mL) and then cooled to an internal reaction mixture temperature of 2° C. Aqueous sodium hydroxide (50% by weight) (43.2 g, 0.541 mol) was added over 10 minutes while maintaining the internal reaction mixture temperature below 14° C. The brown solution was stirred for 1 hour while maintaining the internal reaction mixture temperature below 10° C. 2-(2-Iodo-ethoxy)-2-methyl-propane (87.1 g, 382 mmol) containing 2-methoxy-2-methyl-propane (29 mL) was added over 10 minutes while maintaining the internal reaction mixture temperature between 3 and 5° C. After stirring the green colored reaction mixture at ambient temperature for 16 hours HPLC analysis indicated approximately 20% of unreacted (R)-tert-butoxycarbonylamino-(4-hydroxy-phenyl)-acetic acid present. The reaction mixture was cooled to an internal temperature of 5° C. and additional 2-(2-iodo-ethoxy)-2-methyl-propane (12.1 g, 53.1 mmol) containing 2-methoxy-2-methyl-propane (4 mL) was added over approximately 2 minutes while maintaining an internal reaction mixture temperature of between 5 and 6° C., followed by aqueous sodium hydroxide (50% by weight) (9 g, 113 mmol). The reaction mixture was allowed to warm and stirred at ambient temperature for 2 days. The reaction mixture was cooled to 4° C. and water (1.5 L) added over 1.5 hours while maintaining the internal reaction mixture temperature below 10° C. 2-Methoxy-2-methyl-propane (1.5 L) was added, the reaction mixture partitioned between the 2 phases and the layers separated. The yellow aqueous layer was cooled to 4° C. and 6N aqueous hydrochloric acid (450 mL, 2.7 mol) added over 5 minutes to form a white precipitate. The aqueous mixture was then extracted with ethyl acetate (2×1 L). The combined ethyl acetate extracts were washed with an aqueous solution of ammonium chloride (15% by weight) (175 mL) followed by an aqueous solution of sodium chloride (20% by weight) (175 mL). The reaction mixture was then concentrated under reduced pressure to give (R)-tert-butoxycarbonylamino-[4-(2-tert-butoxy-ethoxy)-phenyl]-acetic acid as a yellow oil which was suitable for further use without additional purification.

Step 1-F: To a suspension of {(R)-[4-(2-tert-butoxyethoxy)-phenyl]-[(S)-1-(5-iodo-1H-benzoimidazol-2-yl)-2-phenyl-ethylcarbamoyl]-methyl}-carbamic acid tert-butyl ester (260 mg, 0.36 mmol) in 6:1 v/v acetonitrile/p-dioxane (14 mL) at 0° C. under an atmosphere of nitrogen was added 4.0 M hydrogen chloride in p-dioxane (420 µL, 1.68 mmol) and the resulting solution stirred at room temperature for 1 hour. Additional 4.0 M hydrogen chloride (420 µL, 1.68 mmol) was added and stirring continued for 30 minutes. The solvent was removed in vacuo and the residue was basified with saturated aqueous sodium hydrogen carbonate solution. The aqueous mixture was extracted with ethyl acetate (2×25 mL), washed with brine, dried over sodium sulfate, filtered and concentrated in vacuo to give (R)-2-amino-2-[4-(2-tert-butoxy-ethoxy)-phenyl]-N-[(S)-1-(5-iodo-1H-benzoimidazol-2-yl)-2-phenyl-ethyl]-acetamide which was used in the subsequent step without further purification (210 mg, 94%).

Step 1-G: To a solution of diphosgene (29 µL, 0.24 mmol) in 1:1 v/v toluene/tetrahydrofuran (20 mL) at −78° C. under an atmosphere of nitrogen was added a solution of (R)-2-amino-2-[4-(2-tert-butoxy-ethoxy)-phenyl]-N-[(S)-1-(5-iodo-1H-benzoimidazol-2-yl)-2-phenyl-ethyl]-acetamide (210 mg, 0.34 mmol) and N,N-diisopropylethylamine (239 µL, 1.37 mmol) in tetrahydrofuran (6 mL) dropwise with stirring. The reaction was allowed to warm to −20° C. then quenched with ice water (10 mL) and stirred for 10 minutes. The mixture was poured into ethyl acetate (30 mL) and the layers were separated. The aqueous layer was extracted with ethyl acetate (20 mL) and the organic extracts were combined, washed with brine, dried over sodium sulfate, filtered and concentrated in vacuo. The crude product was purified by chromatography over silica gel gradient eluted with 20 to 60% v/v ethyl acetate/hexanes to give (R)-5-[4-(2-tert-butoxy-ethoxy)-phenyl]-3-[(S)-1-(5-iodo-1H-benzoimidazol-2-yl)-2-phenyl-ethyl]-imidazolidine-2,4-dione (140 mg, 64%).

HR-MS: calcd for $C_{30}H_{31}IN_4O_4$ [M+H$^+$] 639.1463, found 639.1454.

Step 1-H: To a solution of (R)-5-[4-(2-tert-butoxy-ethoxy)-phenyl]-3-[(S)-1-(5-iodo-1H-benzoimidazol-2-yl)-2-phenyl-ethyl]-imidazolidine-2,4-dione (140 mg, 0.22 mmol) in 1:1 v/v dichloromethane/acetonitrile (2 mL) at 0° C. under an atmosphere of nitrogen was added sodium iodide (62 mg, 0.42 mmol) followed by chlorotrimethylsilane (78 µL, 0.61 mmol), the resulting solution was allowed to stir for 30 minutes. Additional sodium iodide (62 mg, 0.42 mmol) followed by chlorotrimethylsilane (78 µL, 0.61 mmol) was added and stirring continued for a further 45 minutes. The reaction was poured into ethyl acetate (30 mL) and washed with 10% aqueous sodium thiosulfate solution. The organic extract was washed with brine, dried over sodium sulfate, filtered and concentrated in vacuo. The crude product was purified by chromatography over silica gel gradient eluted with 60 to 80% v/v ethyl acetate/hexanes to give (R)-5-[4-(2-hydroxy-ethoxy)-phenyl]-3-[(S)-1-(5-iodo-1H-benzoimidazol-2-yl)-2-phenyl-ethyl]-imidazolidine-2,4-dione (83 mg, 65%).

HR-MS: calcd for $C_{26}H_{23}IN_4O_4$ [M+H$^+$] 583.0837, found 583.0833.

EXAMPLE 2

(R)-5-[4-(2-Hydroxy-ethoxy)-phenyl]-3-(5-iodo-1H-benzoimidazol-2-ylmethyl)-imidazolidine-2,4-dione

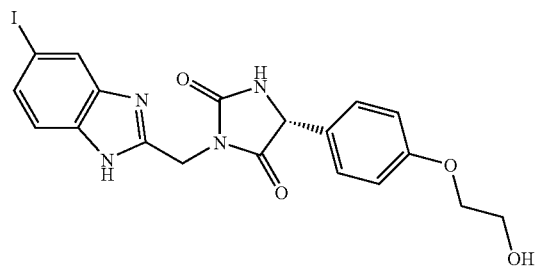

Prepared by the same procedure as described in example 1 except that in step 2-A tert-butoxycarbonylamino-acetic acid was used in place of (S)-2-tert-butoxycarbonylamino-3-phenyl-propionic acid and the resulting fluorocarbonylmethyl-carbamic acid tert-butyl ester was used in place of ((S)-1-fluorocarbonyl-2-phenyl-ethyl)-carbamic acid tert-butyl ester in step 2-B.

HR-MS: calcd for $C_{19}H_{17}IN_4O_4$ [M+H$^+$] 493.0367, found 493.0368.

EXAMPLE 3

(R)-5-[4-(2-Hydroxy-ethoxy)-phenyl]-3-[(S)-1-(5-iodo-1H-benzoimidazol-2-yl)-2-methyl-propyl]-imidazolidine-2,4-dione

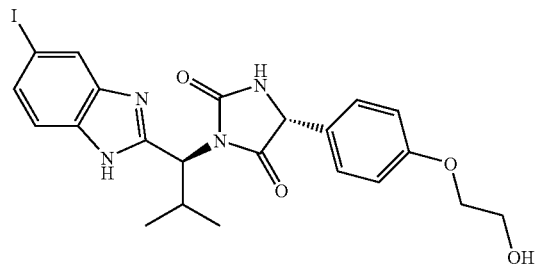

Prepared by the same method as described in example 1 except that steps A and B were replaced by the following procedure (step 3-A) and the product was used in step 3-C.

Step 3-A: To the solution of (S)-2-tert-butoxycarbonylamino-3-methyl-butyric acid (0.33 g, 1.5 mmol), 4-iodo-benzene-1,2-diamine (0.35 g, 1.5 mmol) and diisopropyl-ethyl amine (0.8 mL, 4.5 mmol) in N,N-dimethylformamide (6 mL) was added dropwise a solution of O-benzotriazol-1-yl-N,N, N',N'-tetramethyluronium hexaflurorophosphate (0.71 g, 1.75 mmol) N,N-dimethylformamide (2 mL). The reaction mixture was stirred for 12 hours at room temperature. After adding aqueous sodium carbonate solution, the reaction mixture was extracted with ethyl acetate and the organic layer was washed with aqueous sodium carbonate solution and brine, dried over sodium sulfate, filtered, and concentrated to give a mixture of regioisomers, [(S)-1-(2-amino-4-iodo-phenylcarbamoyl)-2-methyl-propyl]-carbamic acid tert-butyl ester and [(S)-1-(2-amino-5-iodo-phenylcarbamoyl)-2-methyl-propyl]-carbamic acid tert-butyl ester (0.65 g, 100%).

LC-MS: Calcd for $C_{16}H_{24}IN_3O_3$ [M+H$^+$] 434, found 434.
LC-MS: calcd for $C_{22}H_{23}IN_4O_4$ [M+H$^+$] 534, found 534.

EXAMPLE 4

(R)-5-[4-(2-Hydroxy-ethoxy)-phenyl]-3-[(1 R,2R)-1-(5-iodo-1H-benzoimidazol-2-yl)-methoxy-propyl]-imidazolidine-2,4-dione

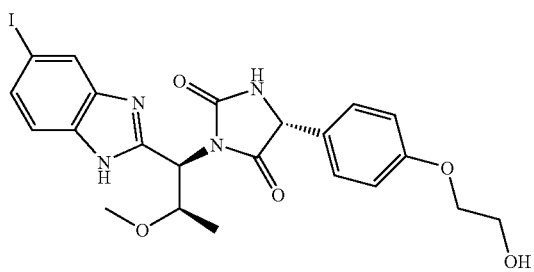

Prepared by the same method as described in example 3 except that in step 4-A (2S,3R)-2-tert-butoxycarbonylamino-3-methoxy-butyric acid was used instead of (S)-2-tert-butoxycarbonylamino-3-methyl-butyric acid.

LC-MS: calcd for $C_{22}H_{23}IN_4O_5$ [M+H$^+$] 551, found 551.

EXAMPLE 5

3-[(S)-1-(5-Iodo-1H-benzoimidazol-2-yl)-2-phenyl-ethyl]-imidazolidine-2,4-dione; compound with trifluoro-acetic acid

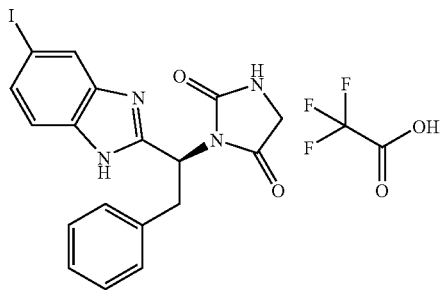

Prepared by the same method as described in example 1 except that (i) in step 5-E tert-butoxycarbonylamino-acetic acid was used in place of (R)-tert-butoxycarbonylamino-[4-(2-tert-butoxy-ethoxy)-phenyl]-acetic acid; (ii) the crude product from step 5-G was purified by preparative reverse phase HPLC chromatography and purified 3-[(S)-1-(5-iodo-1H-benzoimidazol-2-yl)-2-phenyl-ethyl]-imidazolidine-2,4-dione was isolated as the corresponding trifluoroacetate salt, and (iii) step H was omitted.

HR-MS: calcd for $C_{18}H_{15}IN_4O_2$ [M+H$^+$] 447.0313, found 447.0314.

EXAMPLE 6

(R)-3-[(S)-2-(4-Fluoro-phenyl)-1-(5-iodo-1H-benzoimidazol-2-yl)-ethyl]-5-[4-(2-hydroxy-ethoxy)-phenyl]-imidazolidine-2,4-dione

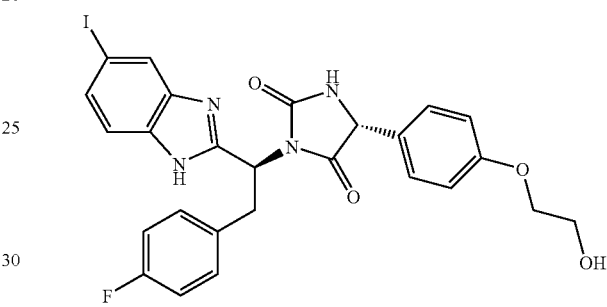

Prepared by the same method as described in example 1 except that in step 6-A (S)-2-tert-butoxycarbonylamino-3-(4-fluoro-phenyl)-propionic acid was used in place of (S)-2-tert-butoxycarbonylamino-3-phenyl-propionic acid.

HR-MS: calcd for $C_{26}H_{22}FIN_4O_4$ [M+H$^+$] 601.0743, found 601.0745.

EXAMPLE 7

(R)-5-[4-(2-Hydroxy-ethoxy)-phenyl]-3-[(S)-1-(5-iodo-1H-benzoimidazol-2-yl)-2-(4-methoxy-phenyl)-ethyl]-imidazolidine-2,4-dione

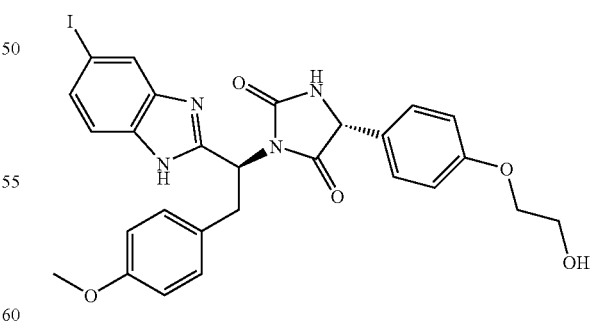

Prepared by the same method as described in example 1 except that in step 7-A (S)-2-tert-butoxycarbonylamino-3-(4-methoxy-phenyl)-propionic acid was used in place of (S)-2-tert-butoxycarbonylamino-3-phenyl-propionic acid.

HR-MS: calcd for $C_{27}H_{25}IN_4O_5$ [M+H$^+$] 613.0943, found 613.0941.

EXAMPLE 8

(R)-5-[4-(2-Hydroxy-ethoxy)-phenyl]-3-[(S)-1-(5-iodo-1H-benzoimidazol-2-yl)-2-thiophen-2-yl-ethyl]-imidazolidine-2,4-dione

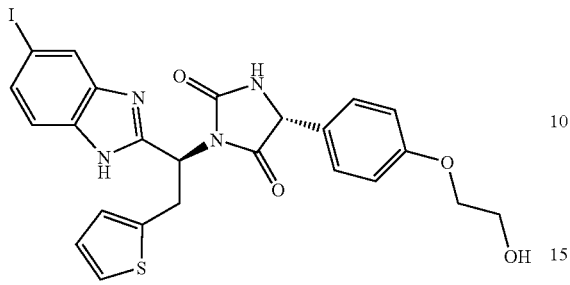

Prepared by the same method as described in example 3 except that in step 8-A (S)-2-tert-butoxycarbonylamino-3-thiophen-2-yl-propionic acid was used in place of (S)-2-tert-butoxycarbonylamino-3-methyl-butyric acid.

LC-MS: calcd for $C_{24}H_{21}IN_4O_4S$ [M+H$^+$] 589, found 589.

EXAMPLE 9

(R)-3-[(1S,2S)-1-(6-Iodo-1H-benzoimidazol-2-yl)-2-phenyl-propyl]-5-phenyl-imidazolidine-2,4-dione

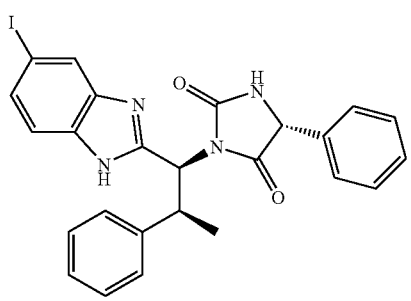

Prepared by the same method as described in example 1 except that (i) (2S,3S)-2-tert-butoxycarbonylamino-3-phenyl-butyric acid was used in place of (S)-2-tert-butoxycarbonylamino-3-phenyl-propionic acid in step 9-A; (ii) (R)-tert-butoxycarbonylamino-phenyl-acetic acid was used in place of (R)-tert-butoxycarbonylamino-[4-(2-tert-butoxy-ethoxy)-phenyl]-acetic acid in step 9-E, and (iii) step H was omitted.

HR-MS: calcd for $C_{25}H_{21}IN_4O_2$ [M+H$^+$] 537.0782, found 537.0780.

EXAMPLE 10

(R)-3-[(1S,2S)-1-(6-Iodo-1H-benzoimidazol-2-yl)-2-phenyl-propyl]-5-(4-methoxy-phenyl)-imidazolidine-2,4-dione

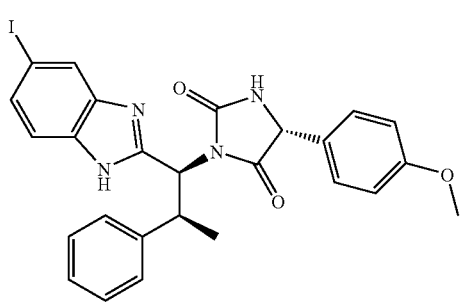

Prepared by the same method as described in example 9 except that in step 10-E (R)-tert-butoxycarbonylamino-(4-methoxy-phenyl)-acetic acid was used in place of (R)-tert-butoxycarbonylamino-[4-(2-tert-butoxy-ethoxy)-phenyl]-acetic acid in step 5. (R)-tert-Butoxycarbonylamino-(4-methoxy-phenyl)-acetic acid was prepared as described in example 14, step 14-K except that iodomethane was used in place of N,N-bis-[2-(tert-butyl-dimethyl-silanyloxy)-ethyl]-2-chloro-acetamide.

HR-MS: calcd for $C_{26}H_{23}IN_4O_3$ [M+H$^+$] 567.0888, found 567.0887.

EXAMPLE 11

(R)-5-[4-(2-Hydroxy-ethoxy)-phenyl]-3-[(1S,2S)-1-(6-iodo-1H-benzoimidazol-2-yl)-2-phenyl-propyl]-imidazolidine-2,4-dione

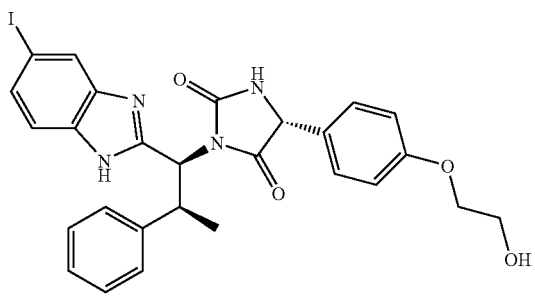

Prepared by the same method as described in example 1 except that in step 11-A (2S,3S)-2-tert-butoxycarbonylamino-3-phenyl-butyric acid was used in place of (S)-2-tert-butoxycarbonylamino-3-phenyl-propionic acid.

HR-MS: calcd for $C_{27}H_{25}IN_4O_4$ [M+H$^+$] 597.0993, found 597.0992.

EXAMPLE 12

(R)-3-[(1S,2S)-1-(6-Iodo-1H-benzoimidazol-2-yl)-2-phenyl-propyl]-5-[4-(2-methoxy-ethoxy-phenyl]-imidazolidine-2,4-dione

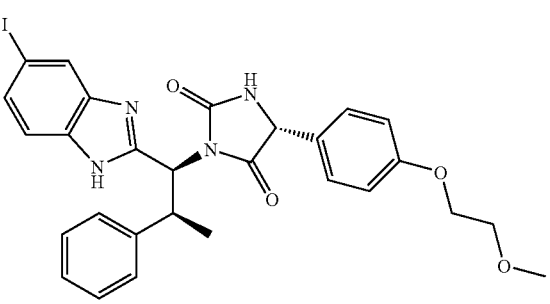

Prepared by the same method as described in example 1 except that (i) (2S,3S)-2-tert-butoxycarbonylamino-3-phenyl-butyric acid was used in place of (S)-2-tert-butoxycarbonylamino-3-phenyl-propionic acid in step 12-A; (ii) (R)-tert-butoxycarbonylamino-[4-(2-methoxy-ethoxy)-phenyl]-acetic acid was used in place of (R)-tert-butoxycarbonylamino-[4-(2-tert-butoxy-ethoxy)-phenyl]-acetic acid in step 12-E, and (iii) step H was omitted. (R)-tert-Butoxycarbonylamino-[4-(2-methoxy-ethoxy)-phenyl]-acetic acid was prepared as described in example 14, step 14-K except that 1-bromo-2-methoxyethane was used in place of N,N-bis-[2-(tert-butyl-dimethyl-silanyloxy)-ethyl]-2-chloro-acetamide.

HR-MS: calcd for $C_{28}H_{27}IN_4O_4$ [M+H$^+$] 611.1150, found 611.1152.

EXAMPLE 13

2-(4-{(R)-1-[(1S,2S)-1-(6-Iodo-1H-benzoimidazol-2-yl)-2-phenyl-propyl]-2,5-dioxo-imidazolidin-4-yl}-phenoxy)-N,N-dimethyl-acetamide

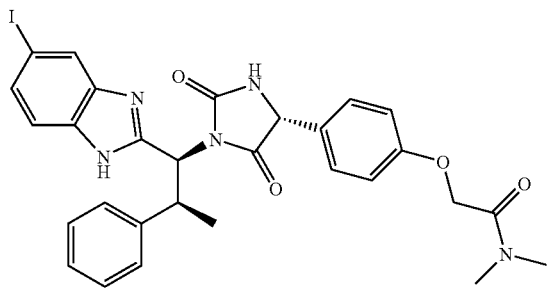

Prepared by the same method as described in example 1 except that (i) (2S,3S)-2-tert-butoxycarbonylamino-3-phenyl-butyric acid was used in place of (S)-2-tert-butoxycarbonylamino-3-phenyl-propionic acid in step 13-A; (ii) (R)-tert-butoxycarbonylamino-(4-dimethylcarbamoylmethoxyphenyl)-acetic acid was used in place of (R)-tert-butoxycarbonylamino-[4-(2-tert-butoxy-ethoxy)-phenyl]-acetic acid in step 13-E, and (iii) step H was omitted. (R)-tert-Butoxycarbonylamino-(4-dimethylcarbamoylmethoxyphenyl)-acetic acid was prepared by the same method as described in example 1, step 1-E for the preparation of (R)-tert-butoxycarbonylamino-[4-(2-tert-butoxy-ethoxy)-phenyl]-acetic acid except that 2-chloro-N,N-dimethyl-acetamide was used in place of 2-(2-iodo-ethoxy)-2-methyl-propane. 2-Chloro-N,N-dimethyl-acetamide was prepared as described in example 14, step 14-J, except that dimethylamine was used in place of bis-[2-(tert-butyl-dimethyl-silanyloxy)-ethyl]amine.

HR-MS: calcd for $C_{29}H_{28}IN_5O_4$ [M+H$^+$] 638.1259, found 638.1260.

EXAMPLE 14

N,N-Bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide

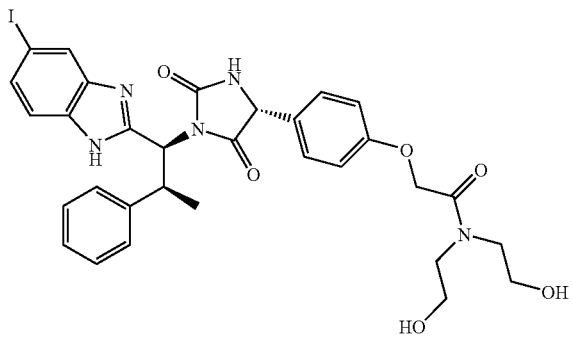

Prepared by the same method as described in example 1 except that (i) (2S,3S)-2-tert-butoxycarbonylamino-3-phenyl-butyric acid was used in place of (S)-2-tert-butoxycarbonylamino-3-phenyl-propionic acid in step 14-A; (ii) (R)-[4-({bis-[2-(tert-butyl-dimethyl-silanyloxy)-ethyl]-carbamoyl}-methoxy)-phenyl]-tert-butoxycarbonylamino-acetic acid (prepared as described below in steps 14-I to 14-K inclusive) was used in place of (R)-tert-butoxycarbonylamino-[4-(2-tert-butoxy-ethoxy)-phenyl]-acetic acid in step 14-E; (iii) deprotection of {[4-({bis-[2-(tert-butyl-dimethyl-silanyloxy)-ethyl]-carbamoyl}-methoxy)-phenyl]-[1-(6-iodo-1H-benzoimidazol-2-yl)-2-phenyl-propylcarbamoyl]-methyl}-carbamic acid tert-butyl ester in step 14-F was performed as described below in step 14-L; (iv) prior to performing the cyclization in step 14-G the diol functionality in 2-amino-2-(4-{[bis-(2-hydroxy-ethyl)-carbamoyl]-methoxy}-phenyl)-N-[1-(6-iodo-1H-benzoimidazol-2-yl)-2-phenyl-propyl]-acetamide was temporarily protected as described below in step 14-M; (v) following the cyclization in step 14-G the diol functionality in N,N-bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide was liberated using the modified work-up procedure described below in step 14-N, and (vi) step H was omitted.

Step 14-I: Diethanolamine (5.0 g, 46.60 mmol), tert-butyldimethylsilyl chloride (14.33 g, 93.20 mmol) and imidazole (6.35 g, 93.20 mmol) were dissolved in dry N,N-dimethylformamide (60 mL) and stirred at ambient temperature for 16 hours. The reaction mixture was then diluted with ethyl acetate (200 mL), washed with saturated aqueous sodium hydrogen carbonate (3×200 mL), saturated brine (200 mL) and the aqueous layers back extracted with ethyl acetate (200 mL). The combined ethyl acetate extracts were dried over sodium sulfate, filtered and concentrated in vacuo to give bis-[2-(tert-butyl-dimethyl-silanyloxy)-ethyl]-amine (10.05 g, 64.5%).

Step 14-J: Choloroacetyl chloride (1.1 g, 9.55 mmol) and potassium carbonate (2.638 g, 19.09 mmol) were dissolved in dry dichloromethane (80 mL) and cooled in an ice salt bath. To this was added bis-[2-(tert-butyl-dimethyl-silanyloxy)-ethyl]amine (3.353 g, 9.545 mmol) in dry dichloromethane (10 mL) over 10 minutes. The reaction mixture was stirred in an ice bath for 2 hours. The mixture was filtered and washed with dichloromethane, then washed with 1.5 N aqueous potassium hydrogen sulfate (2×100 mL) and brine (100 mL). The aqueous layers were back extracted with dichloromethane (2×100 mL), dried over sodium sulfate, filtered and concentrated in vacuo to give N,N-bis-[2-(tert-butyl-dimethyl-silanyloxy)-ethyl]-2-chloro-acetamide (3.8 g, 87.4%).

Step 14-K: (R)-tert-Butoxycarbonylamino-(4-hydroxyphenyl)-acetic acid (1.0 g, 3.741 mmol) was dissolved dry N,N-dimethylformamide (10 mL) and cooled in an ice bath. To this was added portionwise a 60% dispersion of sodium hydride in mineral oil (344 mg, 8.604 mmol). The mixture was then warmed to 10° C. for 0.5 hours, then cooled in an ice bath and N,N-bis-[2-(tert-butyl-dimethyl-silanyloxy)-ethyl]-2-chloro-acetamide (2.13 g, 4.67 mmol) added slowly in dry N,N-dimethylformamide (5 mL). The reaction mixture was warmed to ambient temperature and stirred overnight. Analysis of the reaction mixture by 1H NMR indicated 75% conversion to product. The reaction mixture was cooled in an ice bath and a 60% dispersion of sodium hydride in mineral oil (68 mg, 0.748 mmol) added. After a few minutes N,N-bis-[2-(tert-butyl-dimethyl-silanyloxy)-ethyl]-2-chloro-acetamide (0.46 g, 0.426 mmol) was added. The reaction mixture was warmed to ambient temperature over 1 hour. The reaction mixture was then poured into water (50 mL) and extracted with diethyl ether (2×50 mL). The combined organic extracts were washed with water (50 mL) and brine (50 mL). The organic solution was dried over sodium sulfate, filtered and concentrated in vacuo to give (R)-[4-({bis-[2-(tert-butyl-dimethyl-silanyloxy)-ethyl]-carbamoyl}-methoxy)-phenyl]-tert-butoxycarbonylamino-acetic acid (2.2 g, 45.9%) which was used in step 14-E without further purification.

Step 14-L: {[4-({Bis-[2-(tert-butyl-dimethyl-silanyloxy)-ethyl]-carbamoyl}-methoxy)-phenyl]-[1-(6-iodo-1H-benzoimidazol-2-yl)-2-phenyl-propylcarbamoyl]-methyl}-carbamic acid tert-butyl ester (270 mg, 0.27 mmol) was dissolved in dry dichloromethane (6 mL) and cooled in an ice bath. To the stirred solution was added triflouroacetic acid (3.12 mL, 40.5 mmol). The reaction mixture was stirred at 0° C. for 1 hour. The reaction mixture was concentrated in vacuo, dissolved in dichloromethane (1 mL) and the crude trifluoroacetate salt precipitated with ether (5 mL) and pentane (10 mL). The precipitate was triturated then filtered. The solid was taken into dichloromethane (50 mL) and tetrahydrofuran added to form a clear solution. The solution was washed with saturated aqueous sodium hydrogen carbonate (2×50 mL), the layers separated and the aqueous layer extracted with dichloromethane (4×50 mL). The combined organic extracts were dried over sodium sulfate filtered and concentrated in vacuo. The resulting solid was triturated with a mixture of ether (1 mL) and pentane (5 mL), filtered and dried to give (R)-2-amino-2-(4-{[bis-(2-hydroxy-ethyl)-carbamoyl]-methoxy}-phenyl)-N-[(1S,2S)-1-(6-iodo-1H-benzoimidazol-2-yl)-2-phenyl-propyl]-acetamide (170 mg, 93.8%).

Step 14-M: (R)-2-Amino-2-(4-{[bis-(2-hydroxy-ethyl)-carbamoyl]-methoxy}-phenyl)-N-[(1S,2S)-1-(6-iodo-1H-benzoimidazol-2-yl)-2-phenyl-propyl]-acetamide (170 mg, 0.253 mmol) was dissolved in dry tetrahydrofuran (3.4 mL) and cooled in an ice bath. To this solution was added triethylamine (176.3 μL, 1.265 mmol) followed by trimethylsilyl chloride (132 μL, 1.012 mmol). After 0.5 hours another 2.5 equivalents of triethylamine (88 μL, 0.63 mmol) and 2 equivalents of trimethylsilyl chloride (66 μL, 0.506 mmol) were added. The reaction mixture was stirred at 0° C. for an additional 1.5 hours then the reaction mixture was poured into ethyl acetate (40 mL) and washed with brine (3×25 mL). The combine aqueous washes were then extracted with ethyl acetate (2×25 mL). The combined organic extracts were dried over sodium sulfate, filtered and concentrated in vacuo to give (R)-2-amino-2-(4-{[bis-(2-trimethylsilanyloxy-ethyl)-carbamoyl]-methoxy}-phenyl)-N-[(1S,2S)-1-(6-iodo-1H-benzoimidazol-2-yl)-2-phenyl-propyl]-acetamide (190 mg, 92%).

Step 14-N: After cyclization of (R)-2-amino-2-(4-{[bis-(2-trimethylsilanyloxy-ethyl)-carbamoyl]-methoxy}-phenyl)-N-[(1S,2S)-1-(6-iodo-1H-benzoimidazol-2-yl)-2-phenyl-propyl]-acetamide with diphosgene was complete and the reaction mixture had been partitioned between ethyl acetate and ice/water (as described in example 1, step 1-G) 1N aqueous hydrochloric acid (20 mL) was added to the ethyl acetate extracts and the mixture was stirred at ambient temperature for 15 minutes. The layers were separated and the aqueous layer was extracted with ethyl acetate (2×50 mL) and washed with brine (50 mL). The combined organic layers were dried over sodium sulfate, filtered and concentrated in vacuo. The crude product was purified by gradient flash chromatography using silica gel eluted with from 0 to 10% v/v methanol in dichloromethane. The product containing fractions were combined and concentrated to give a solid which was triturated with a 1:1 v/v mixture of dichloromethane/ether (1 mL). The suspension was stirred for 1 hour then filtered and dried to give N,N-bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide (30 mg, 27.7%).

HR-MS: calcd for $C_{31}H_{32}IN_5O_6$ [M+H$^+$] 698.1470, found 698.1468.

EXAMPLE 15

(R)-3-[(1S,2S)-1-(5-Iodo-1H-benzoimidazol-2-yl)-2-phenyl-propyl]-5-isopropyl-imidazolidine-2,4-dione

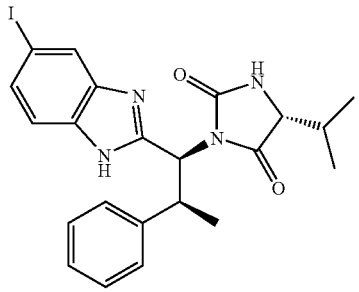

Prepared by the same method as described in example 9 except that in step 15-E (R)-2-tert-butoxycarbonylamino-3-methyl-butyric acid was used in place of (R)-tert-butoxycarbonylamino-phenyl-acetic acid.

HR-MS: calcd for $C_{22}H_{23}IN_4O_2$ [M+H$^+$] 503.0939, found 503.0936.

EXAMPLE 16

(R)-5-Cyclohexyl-3-[(1S,2S)-1-(5-iodo-1H-benzoimidazol-2-yl)-2-phenyl-propyl]-imidazolidine-2,4-dione

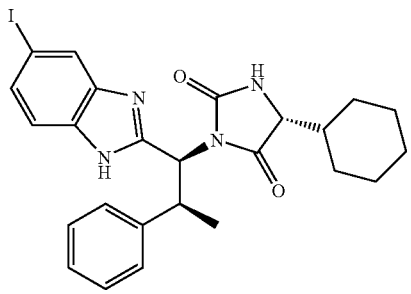

Prepared by the same method as described in example 9 except that in step 16-E (R)-tert-butoxycarbonylamino-cyclohexyl-acetic acid was used in place of (R)-tert-butoxycarbonylamino-phenyl-acetic acid.

HR-MS: calcd for $C_{25}H_{27}IN_4O_2$ [M+H$^+$] 543.1252, found 543.1252.

EXAMPLE 17

(R)-5-[4-(2-Hydroxy-ethoxy)-phenyl]-3-[1-(5-iodo-1H-benzoimidazol-2-yl)-cyclopropyl]-imidazolidine-2,4-dione

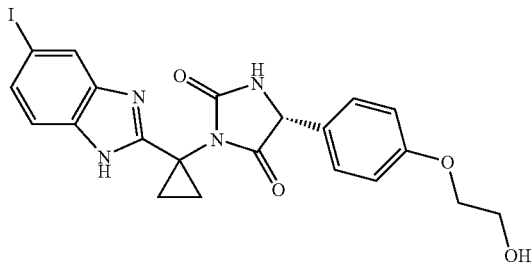

Prepared by the same method as described in example 1 except that in step 17-A 1-tert-butoxycarbonylamino-cyclopropanecarboxylic acid was used in place of (S)-2-tert-butoxycarbonylamino-3-phenyl-propionic acid.

HR-MS: calcd for $C_{21}H_{19}IN_4O_4$ [M+H$^+$] 519.0524, found 519.0522.

EXAMPLE 18

(R)-3-[(1S,2S)-1-(6-Bromo-1H-benzoimidazol-2-yl)-2-phenyl-propyl]-5-[4-(2-hydroxy-ethoxy)-phenyl]-imidazolidine-2,4-dione

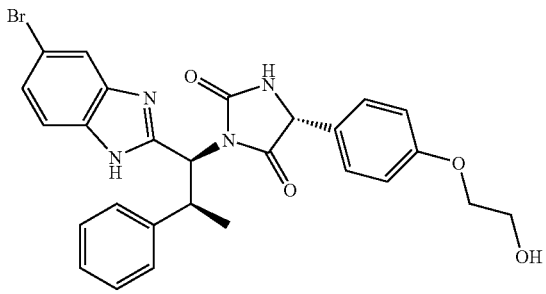

Prepared by the same method as described in example 11 except that in step 18-B 4-bromo-benzene-1,2-diamine was used in place of 4-iodo-benzene-1,2-diamine.

HR-MS: calcd for $C_{27}H_{25}BrN_4O_4$ [M+H$^+$] 549.1132, found 549.1132.

EXAMPLE 19

(R)-3-[(S)-1-(5-Cyclopropyl-1H-benzoimidazol-2-yl)-2-phenyl-ethyl]-5-[4-(2-hydroxy-ethoxy)-phenyl]-imidazolidine-2,4-dione

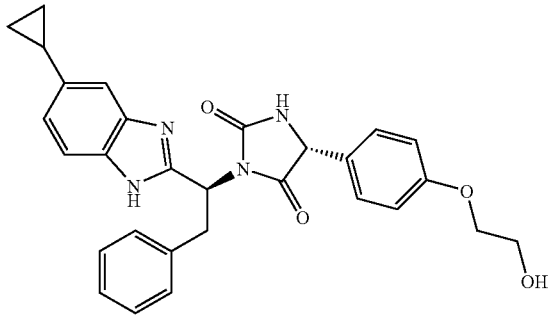

Prepared by the same method as described in example 1 except that 4-cyclopropyl-benzene-1,2-diamine was used in place of 4-iodo-benzene-1,2-diamine in step 19-B. 4-Cyclopropyl-benzene-1,2-diamine was prepared as described below in steps 19-I and 19-J.

Step 19-I: 4-Bromo-2-nitroaniline (2.17 g, 10 mmol), cyclopropylboronic acid (1.12 g, 1.30 mmol), potassium phosphate (7.42 g, 35 mmol), palladium (II) acetate (120 mg, 0.5 mmol), and cyclohexylphosphine (280 mg, 1 mmol) were combined in toluene (40 mL) and water (2 mL) and heated on an oil bath at 100° C. for 16 hours. The mixture was cooled, and the mixture was triturated with dichloromethane and water. The resulting mixture was filtered through a pad of celite. The organic layer of the filtrate was separated and dried over anhydrous sodium sulfate. Concentration gave an oil that was chromatographed over silica gel (30% v/v diethyl ether in hexanes). The faster moving compound was collected and the solvent was concentrated to give an orange oil. The oil was dissolved in hot hexanes/ethyl acetate and cooling gave 4-cyclopropyl-2-nitroaniline as orange needles (333 mg, 1.87 mmol, 19%).

$^1$H NMR (300 MHz, CDCl$_3$) $\delta_H$ 7.81 (s, 1H), 7.13 (d, 1H), 6.70 (d, 1H), 5.91 (br s, 2H), 1.81 (m, 1H), 0.90 (m, 2H), 0.61 (m, 2H) ppm.

Step 19-J: 4-Cyclopropyl-2-nitroaniline (178 mg, 1 mmol) was dissolved in absolute methanol (6 mL), and zinc powder (200 mg, 3.1 mmol) and ammonium chloride (800 mg, 15 mmol) were added. The mixture was stirred at room temperature for 16 hours. The mixture was filtered through a pad of celite, and the filtrate was concentrated in vacuo. The residue was partitioned between water (30 mL) and dichloromethane (30 mL). The organic layer was separated, and the aqueous layer was extracted twice with dichloromethane (15 mL). The combined organic layers were dried over anhydrous sodium sulfate and concentrated in vacuo to give 4-cyclopropyl-benzene-1,2-diamine as a brown solid which was used without further purification (130 mg, 88%).

$^1$H NMR (300 MHz, CDCl$_3$) $\delta_H$ 6.61 (d, 1H), 6.46 (m, 1H), 3.10 (br s, 4H), 1.76 (m, 1H), 0.84 (m, 2H), 0.58 (m, 2H) ppm.

HR-MS: calcd for $C_{29}H_{28}N_4O_4$ [M+H$^+$] 497.2184, found 497.2182.

EXAMPLE 20

(R)-3-[(S)-1-(5-Ethynyl-1H-benzoimidazol-2-yl)-2-phenyl-ethyl]-5-[4-(2-hydroxy-ethoxy)-phenyl]-imidazolidine-2,4-dione

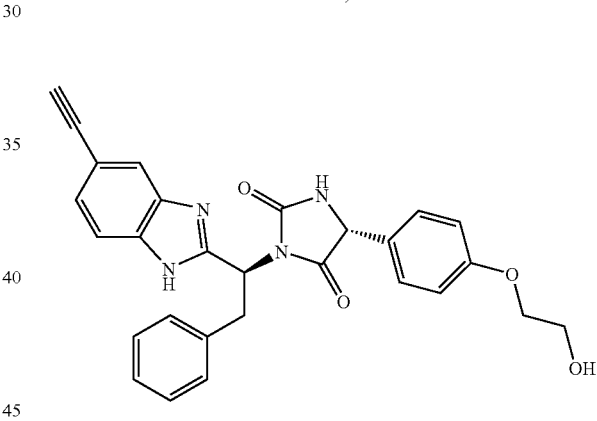

Prepared by the same method as described in example 1 except that after performing step 20-C, and prior to performing step 20-D, the following 2 steps (steps 20-I and step 20-J) were performed.

Step 20-I: A solution of [(S)-1-(5-iodo-1H-benzoimidazol-2-yl)-2-phenyl-ethyl]-carbamic acid tert-butyl ester (100 mg, 0.216 mmol), copper (I) iodide (8 mg, 0.043 mmol) and dichlorobis(triphenylphosphine)palladium (II) (15 mg, 0.022 mmol) in N,N-dimethylformamide (7 mL) in a sealed tube apparatus was degassed with dry nitrogen. The yellow mixture was stirred at room temperature for an additional 5 minutes, then triethylamine (90 µL, 0.648 mmol) and trimethylsilylacetylene (92 µL, 0.648 mmol) were added, and the resulting solution was degassed once more After stirring the reaction mixture for 5 minutes at room temperature a deep red to black solution resulted. This mixture was left to stir overnight at room temperature then poured into a separatory funnel containing water (50 mL) and ethyl acetate (50 mL). The aqueous layer was separated and extracted twice with ethyl acetate (20 mL). The combined organic layers were dried over sodium sulfate, filtered and concentrated in vacuo. The residue was applied to a silica gel column using dichloromethane (10 mL) and gradient eluted from 10 to 100% v/v ethyl acetate in hexanes to give [(S)-2-phenyl-1-(6-trimethylsilanylethynyl-1H-benzoimidazol-2-yl)-ethyl]-carbamic acid tert-butyl ester (90 mg, 96%).

Step 20-J: To a solution of [(S)-2-Phenyl-1-(6-trimethylsilanylethynyl-1H-benzoimidazol-2-yl)-ethyl]-carbamic acid tert-butyl ester (90 mg, 0.208 mmol) in methanol (10 mL) at room temperature, was added finely powdered anhydrous potassium carbonate (258 mg, 1.87 mmol). The resulting heterogenous mixture was stirred at room temperature until LC/MS indicated the reaction was complete. The solvent was then allowed to evaporate and resulting residue was partitioned in 1:1 v/v water/ethyl acetate (50 mL total volume) and the aqueous layer was separated and extracted twice with ethyl acetate (20 mL). The combined organic layers were dried over sodium sulfate, filtered and concentrated in vacuo. The yellowish colored residue was applied to a silica gel column using dichloromethane (10 mL) and gradient eluted from 10 to 75% v/v ethyl acetate in hexanes to give [(S)-1-(6-ethynyl-1H-benzoimidazol-2-yl)-2-phenyl-ethyl]-carbamic acid tert-butyl ester (54 mg, 72%)

HR-MS: calcd for $C_{28}H_{24}N_4O_4$ [M+H$^+$] 481.1871, found 481.1870.

EXAMPLE 21

(R)-3-[(1S,2S)-1-(5-Ethynyl-1H-benzoimidazol-2-yl)-2-phenyl-propyl]-5-[4-(2-hydroxy-ethoxy)-phenyl]-imidazolidine-2,4-dione

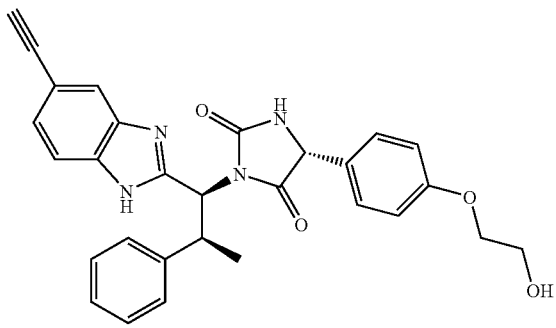

Prepared by the same method as described in example 20 except that in step 21-A (2S,3S)-2-tert-butoxycarbonylamino-3-phenyl-butyric acid was used in place of (S)-2-tert-butoxycarbonylamino-3-phenyl-propionic acid.

HR-MS: calcd for $C_{29}H_{26}N_4O_4$ [M+H$^+$] 495.2027, found 495.2028.

What is claimed is:
1. A compound of formula I

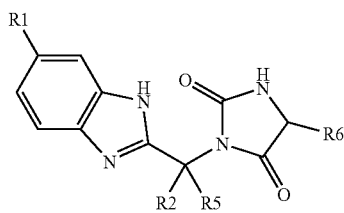

I where:
R1 is selected from the group consisting of halogen, ethynyl, and cycloalkyl,
R2 is selected from the group consisting of hydrogen and CH(R3)(R4);
R3 is selected from the group consisting of lower alkyl, lower alkoxy, optionally substituted aryl, and optionally substituted heteroaryl;
R4 is selected from the group consisting of hydrogen and lower alkyl;
R5 is hydrogen or, taken together with R2 and the carbon to which R2 and R5 are attached, forms lower cycloalkyl;
R6 is selected from the group consisting of hydrogen, lower alkyl, lower cycloalkyl, optionally substituted aryl, and optionally substituted heteroaryl;
and pharmaceutically acceptable salts or esters thereof.

2. A compound claim 1 where:
R1 is selected from the group consisting of bromo, iodo, ethynyl, and C3 to C6 cycloalkyl,
R2 is selected from the group consisting of hydrogen and CH(R3)(R4);
R3 is selected from the group consisting of C1 to C3 alkyl, C1 to C3 alkoxy, optionally substituted phenyl, and optionally substituted heteroaryl, wherein the heteroaryl group contains at least one sulfur atom or nitrogen atom;
R4 is selected from the group consisting of hydrogen and C1 to C3 alkyl;
R5 is hydrogen or, taken together with R2 and the carbon to which R2 and R5 are attached, forms lower cycloalkyl;
R6 is selected from the group consisting of hydrogen, lower alkyl, lower cycloalkyl, optionally substituted aryl, and optionally substituted heteroaryl;
and pharmaceutically acceptable salts or esters thereof.

3. A compound of claim 1 where R1 is selected from the group consisting of iodo, bromo, ethynyl, and cyclopropyl.

4. A compound of claim 1 where R2 is CH(R3)(R4) and R3 is selected from the group consisting of methyl, methoxy, phenyl, 4-fluorophenyl, 4-methoxyphenyl, and thiophene.

5. A compound of claim 4 where R2 is CH(R3)(R4) and R4 is selected from the group consisting of hydrogen and methyl.

6. A compound of claim 1 where R5, taken together with R2 and the carbon to which R2 and R5 are attached, forms lower cycloalkyl.

7. A compound of claim 6 where R5, taken together with R2 and the carbon to which R2 and R5 are attached, forms cyclopropyl.

8. A compound of claim 1 where R6 is selected from the group consisting of 2-propyl, cyclohexyl, phenyl, 4-methoxyphenyl, 4-(O(CH2)2OH)-phenyl, 4-(O(CH2)2OCH3)-phenyl, 4-(OCH2C(O)N(CH3)2)-phenyl, and 4-(OCH2C(O)N((CH2)2OH)2)-phenyl.

9. A compound of claim 1 wherein:
R1 is selected from the group consisting of cyclopropyl, acetylene, I, and Br;
R2 is selected from the group consisting of hydrogen and CH(R3)(R4);
R3 is selected from the group consisting of methyl, methoxy, phenyl, 4-fluorophenyl, 4-methoxyphenyl, and 2-thiophenyl;
R4 is selected from the group consisting of hydrogen and methyl;
R5 is hydrogen or, taken together with R2 and the carbon to which R2 and R5 are attached, is cyclopropyl;
R6 is selected from the group consisting of hydrogen, 2-propyl, cyclohexyl, phenyl, 4-methoxyphenyl, 4-(O (CH2)2OH)-phenyl, 4-(O(CH2)2OCH3)-phenyl, 4-(OCH2C(O)N(CH3)2)-phenyl, and 4-(OCH2C(O)N((CH2)2OH)2)-phenyl.

10. A compound selected from the group consisting of:
- (R)-5-[4-(2-Hydroxy-ethoxy)-phenyl]-3-[(S)-1-(6-iodo-1H-benzoimidazol-2-yl)-2-phenyl-ethyl]-imidazolidine-2,4-dione;
- (R)-5-[4-(2-Hydroxy-ethoxy)-phenyl]-3-(5-iodo-1H-benzoimidazol-2-ylmethyl)-imidazolidine-2,4-dione;
- (R)-5-[4-(2-Hydroxy-ethoxy)-phenyl]-3-[(S)-1-(5-iodo-1H-benzoimidazol-2-yl)-2-methyl-propyl]-imidazolidine-2,4-dione;
- (R)-5-[4-(2-Hydroxy-ethoxy)-phenyl]-3-[(1R,2R)-1-(5-iodo-1H-benzoimidazol-2-yl)-2-methoxy-propyl]-imidazolidine-2,4-dione;
- 3-[(S)-1-(5-Iodo-1H-benzoimidazol-2-yl)-2-phenyl-ethyl]-imidazolidine-2,4-dione; compound with trifluoro-acetic acid;
- (R)-3-[(S)-2-(4-Fluoro-phenyl)-1-(5-iodo-1H-benzoimidazol-2-yl)-ethyl]-5-[4-(2-hydroxy-ethoxy)-phenyl]-imidazolidine-2,4-dione;
- (R)-5-[4-(2-Hydroxy-ethoxy)-phenyl]-3-[(S)-1-(5-iodo-1H-benzoimidazol-2-yl)-2-(4methoxy-phenyl)-ethyl]-imidazolidine-2,4-dione;
- (R)-5-[4-(2-Hydroxy-ethoxy)-phenyl]-3-[(S)-1-(5-iodo-1H-benzoimidazol-2-yl)-2-thiophen-2-yl-ethyl]-imidazolidine-2,4-dione;
- (R)-3-[(1S,2S)-1-(6-Iodo-1H-benzoimidazol-2-yl)-2-phenyl-propyl]-5-phenyl-imidazolidine-2,4-dione;
- (R)-3-[(1S,2S)-1-(6-Iodo-1H-benzoimidazol-2-yl)-2-phenyl-propyl]-5-(4-methoxy-phenyl)-imidazolidine-2,4-dione;
- (R)-5-[4-(2-Hydroxy-ethoxy)-phenyl]-3-[(1S,2S)-1-(6-iodo-1H-benzoimidazol-2-yl)-2-phenyl-propyl]-imidazolidine-2,4-dione;
- (R)-3-[(1S,2S)-1-(6-Iodo-1H-benzoimidazol-2-yl)-2-phenyl-propyl]-5-[4-(2-methoxy-ethoxy)-phenyl]-imidazolidine-2,4-dione;
- 2-(4-{(R)-1-[(1S,2S)-1-(6-Iodo-1H-benzoimidazol-2-yl)-2-phenyl-propyl]-2,5-dioxo-imidazolidin-4-yl}-phenoxy)-N,N-dimethyl-acetamide;
- N,N-Bis-(2-hydroxy-ethyl)-2-(4-{(R)-1-[(1S,2S)-1-(6-iodo-1H-benzoimidazol-2-yl)-2-phenyl-propyl]-2,5-dioxo-imidazolidin-4-yl}-phenoxy)-acetamide;
- (R)-3-[(1S,2S)-1-(5-Iodo-1H-benzoimidazol-2-yl)-2-phenyl-propyl]-5-isopropyl-imidazolidine-2,4-dione;
- (R)-5-Cyclohexyl-3-[(1S,2S)-1-(5-iodo-1H-benzoimidazol-2-yl)-2-phenyl-propyl]-imidazolidine-2,4-dione;
- (R)-5-[4-(2-Hydroxy-ethoxy)-phenyl]-3-[1-(5-iodo-1H-benzoimidazol-2-yl)-cyclopropyl]-imidazolidine-2,4-dione;
- (R)-3-[(1S,2S)-1-(6-Bromo-1H-benzoimidazol-2-yl)-2-phenyl-propyl]-5-[4-(2-hydroxy-ethoxy)-phenyl]-imidazolidine-2,4-dione;
- (R)-3-[(S)-1-(5-Cyclopropyl-1H-benzoimidazol-2-yl)-2-phenyl-ethyl]-5-[4-(2-hydroxy-ethoxy)-phenyl]-imidazolidine-2,4-dione;
- (R)-3-[(S)-1-(5-Ethynyl-1H-benzoimidazol-2-yl)-2-phenyl-ethyl]-5-[4-(2-hydroxy-ethoxy)-phenyl]-imidazolidine-2,4-dione; and
- (R)-3-[(1S,2S)-1-(5-Ethynyl-1H-benzoimidazol-2-yl)-2-phenyl-propyl]-5-[4-(2-hydroxy-ethoxy)-phenyl]-imidazolidine-2,4-dione.

\* \* \* \* \*